(12) United States Patent
Ufkes

(10) Patent No.: US 10,556,025 B2
(45) Date of Patent: Feb. 11, 2020

(54) FIXED POSITION HYBRID GERMICIDAL IRRADIATION APPARATUS, METHOD, AND SYSTEM

(71) Applicant: UD Innovations, LLC, Sullivan's Island, SC (US)

(72) Inventor: Philip J. Ufkes, Sullivan's Island, SC (US)

(73) Assignee: UD Innovations, LLC, Sullivan's Island, SC (US)

( * ) Notice: Subject to any disclaimer, the term of this patent is extended or adjusted under 35 U.S.C. 154(b) by 136 days.

(21) Appl. No.: 15/869,417

(22) Filed: Jan. 12, 2018

(65) Prior Publication Data

US 2018/0193501 A1  Jul. 12, 2018

Related U.S. Application Data

(60) Provisional application No. 62/445,415, filed on Jan. 12, 2017.

(51) Int. Cl.
*A61L 2/10* (2006.01)
*A61L 2/24* (2006.01)

(52) U.S. Cl.
CPC ...... *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC ..... A61L 2/10; A61L 2/28; A61L 2/24; A61L 2202/25; A61B 90/70
See application file for complete search history.

(56) References Cited

U.S. PATENT DOCUMENTS 5,628,303 A   5/1997  Ahmady et al.
6,078,425 A   6/2000  Wolfe et al.
(Continued)

FOREIGN PATENT DOCUMENTS

DE   202014001022 U1   5/2015
WO      2016069701 A1   5/2016

OTHER PUBLICATIONS

Indigo-Clean (2016) (Year: 2016).*
(Continued)

*Primary Examiner* — Sean E Conley
*Assistant Examiner* — Brendan A Hensel
(74) *Attorney, Agent, or Firm* — Gregory Finch; Finch Paolino, LLC

(57) ABSTRACT

A fixed position hybrid germicidal irradiation apparatus, method, and system for ultraviolet germicidal irradiation. A plurality of emitters may be coupled to a substantially rectangular housing configured to be coupled to a standard commercial lighting fitting. A second plurality of emitters may be coupled to the substantially rectangular housing. The first plurality of emitters and the second plurality of emitters are operable to emit UV-C radiation at a wavelength of about 265 nanometers and near-UV radiation at a wavelength of about 405 nanometers respectively. UV-C sensors are configured to measure the amount of UV-C light or near UV-C light from a target surface. A controller may be configured to engage with the UV-C sensors to determine the amount of UV-C radiation collected by the UV-C sensors. The improved apparatus, method, and system reduces exposure time by varying the intensity and wavelength of the UV administered, while concurrently reducing UV overexposure.

20 Claims, 7 Drawing Sheets

(56) References Cited

U.S. PATENT DOCUMENTS

| | | |
|---|---|---|
| 6,656,424 B1 | 12/2003 | Deal |
| 6,911,177 B2 | 6/2005 | Deal |
| 7,175,806 B2 | 2/2007 | Deal et al. |
| 7,459,694 B2 | 12/2008 | Scheir et al. |
| 7,754,156 B2 | 7/2010 | Hyde et al. |
| 7,763,212 B2 | 7/2010 | McEllen |
| 7,829,016 B2 | 11/2010 | Deal et al. |
| 8,067,750 B2 | 11/2011 | Deal |
| 8,114,342 B2 | 2/2012 | Jung et al. |
| 8,178,042 B2 | 5/2012 | Jung et al. |
| 8,226,887 B2 | 7/2012 | Harmon et al. |
| 8,398,264 B2 | 3/2013 | Anderson et al. |
| 8,455,832 B2 | 6/2013 | Statham et al. |
| 8,575,567 B2 | 11/2013 | Lyslo et al. |
| 8,584,612 B2 | 11/2013 | Hart et al. |
| 8,859,994 B2 | 10/2014 | Deal |
| 8,932,535 B2 | 1/2015 | Hyde et al. |
| 9,039,966 B2 | 5/2015 | Anderson et al. |
| 9,205,162 B2 | 12/2015 | Deal et al. |
| 9,358,313 B2 | 6/2016 | Deal |
| 9,370,600 B1 | 6/2016 | DuPuis et al. |
| 9,657,177 B1 | 5/2017 | Pringle et al. |
| 2002/0192361 A1 | 12/2002 | Chang et al. |
| 2006/0215257 A1 | 9/2006 | Morrow et al. |
| 2007/0023710 A1 | 2/2007 | Tom et al. |
| 2008/0019861 A1 | 1/2008 | Silderhuis |
| 2010/0060194 A1 | 3/2010 | Furry et al. |
| 2012/0121457 A1 | 5/2012 | Farren |
| 2012/0126134 A1* | 5/2012 | Deal .................. A61L 2/10 250/372 |
| 2012/0308784 A1 | 12/2012 | Chen |
| 2013/0330235 A1 | 12/2013 | Stibich et al. |
| 2014/0044590 A1 | 2/2014 | Trapani |
| 2014/0131595 A1 | 5/2014 | Nathan et al. |
| 2015/0062893 A1 | 3/2015 | Lynn et al. |
| 2015/0086420 A1 | 3/2015 | Trapani |
| 2015/0217012 A1* | 8/2015 | Garner .................. A61L 2/10 422/24 |
| 2015/0250914 A1 | 9/2015 | Aeifin et al. |
| 2016/0046839 A1 | 2/2016 | Maruno et al. |
| 2016/0058020 A1 | 3/2016 | Shur et al. |
| 2016/0067365 A1 | 3/2016 | Ma et al. |
| 2016/0219859 A1 | 8/2016 | Deal |
| 2016/0271281 A1 | 9/2016 | Clynne et al. |
| 2016/0271803 A1 | 9/2016 | Stewart |
| 2016/0296649 A1 | 10/2016 | Ramanand et al. |
| 2016/0375166 A1 | 12/2016 | Kreitenberg |

OTHER PUBLICATIONS

International search report, International application No. PCT/US2018/016666, dated Jun. 8, 2018. ISA/US, Alexandria, VA.

Rutala, W. et al., "Rapid Hospital Room Decontamination Using Ultraviolet (UV) Light with a Nanostructured UV-Reflective Wall Coating." Infection Control and Hospital Epidemiology. vol. 34, No. 5, pp. 527-529. May 2013. Cambridge University Press, Cambridge, UK.

Indigo-Clean. 3 pages. Accessed online Jan. 11, 2018 at https://Kenall.com/Indigo-Clean. Kenall, Kenosha, WI.

International search report, International application No. PCT/US2018/013528, dated Mar. 28, 2018. ISA/US, Alexandria, VA.

International search report, International application No. PCT/US2018/013516, dated Apr. 4, 2018. ISA/US, Alexandria, VA.

Indigo-Clean. 5 pages. Jan. 2016. Accessed at https://web.archive.org/web/20160118200700/http://indigo-clean.com/what-is-it.

* cited by examiner

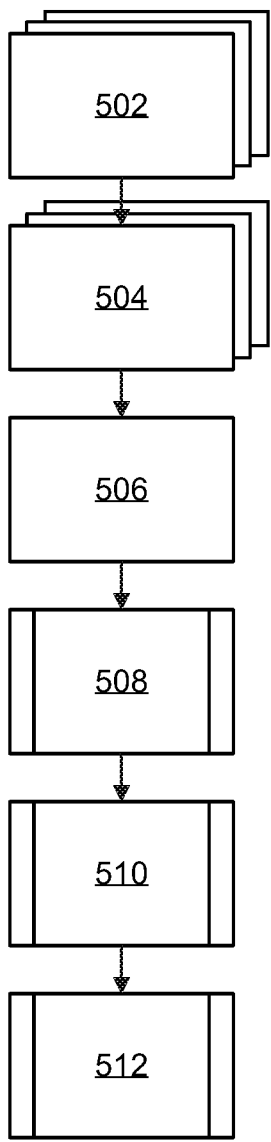
Fig. 8
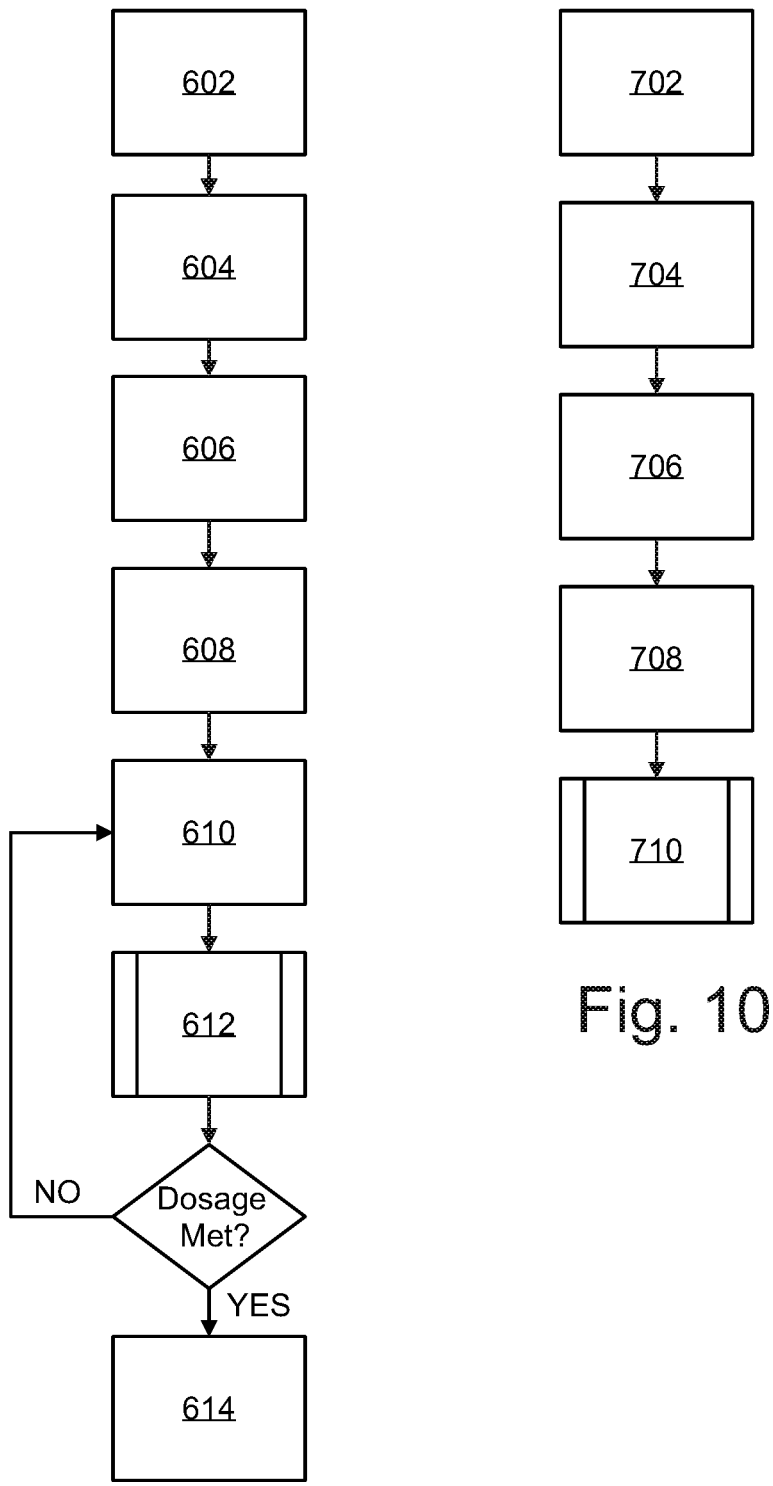
Fig. 9
Fig. 10

FIXED POSITION HYBRID GERMICIDAL IRRADIATION APPARATUS, METHOD, AND SYSTEM

CROSS-REFERENCE TO RELATED APPLICATIONS

This application claims the benefit of U.S. Provisional Application Ser. No. 62/445,415, filed on Jan. 12, 2017 entitled "FIXED POSITION HYBRID GERMICIDAL IRRADIATION APPARATUS, METHOD AND SYSTEM", the disclosure of which is hereby incorporated in its entirety at least by reference.

BACKGROUND OF THE INVENTION

1. Field of the Invention

This invention relates to methods and devices for bacterial, fungal and/or viral sterilization and disinfection, and is more particularly directed to a UV-C disinfection apparatus and system for ultraviolet and near-ultraviolet germicidal irradiation.

2. Description of Related Art

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm. UV-C LEDs use semiconductors to emit light between 255 nm-280 nm. The wavelength emission is tunable by adjusting the material of the semiconductor. The use of LEDs that emit a wavelength more precisely tuned to the maximal germicidal wavelength results in greater microbe deactivation per amp of power, maximization of microbial deactivation for the available, less ozone production, and less materials degradation. Embodiments of the present disclosure provide for a disinfection fixture that reduces exposure time by varying the intensity and wavelength of the UV-C administered. Like UVGI, near-UV (violet-blue) light, particularly 405 nm light, has significant antimicrobial properties against a wide range of bacterial and fungal pathogens. Unlike UVGI, near-UV is safe for continuous use in occupied environments. Consequently, a hybrid arrangement allows for the optimum deployment of both UVGI and near-UV in a closed-loop disinfection process and also provides general area illumination.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is a mounted, typically ceiling mounted, hybrid germicidal irradiation disinfection apparatus comprising a substantially rectangular housing having dimensions of approximately two feet in width and four feet in length; a first plurality of emitters coupled to the substantially rectangular housing, the first plurality of emitters operable to emit UV-C radiation at a wavelength of about 265 nanometers; a second plurality of emitters coupled to the substantially rectangular housing, the second plurality of emitters operable to emit near-UV radiation at a wavelength of about 405 nanometers; at least one visible light emitter coupled to the substantially rectangular housing; at least one germicidal radiation sensor coupled to the substantially planar array surface; a controller being housed in the substantially rectangular housing, the controller being operably engaged with the first plurality of emitters, the second plurality of emitters, the at least one visible light emitter, and the at least one germicidal radiation sensor.

Another object of the present disclosure is a method for room disinfection using germicidal radiation comprising: installing, in an interior ceiling grid, a hybrid germicidal irradiation disinfection apparatus (disinfection fixture), the disinfection fixture having a first plurality of emitters operable to emit UV-C radiation at a wavelength of about 265 nanometers and a second plurality of emitters operable to emit near-UV radiation at a wavelength of about 405 nanometers, a ranging sensor, and a controller; measuring, with the ranging sensor, the distance to the closest object (surface) in the room; calculating, with the controller, an air gap compensation variable in response to ranging sensor measurement; delivering, with the first plurality of emitters and the second plurality of emitters, dual band radiation to a target zone of the room; receiving, with at least one germicidal radiation sensor, an amount of radiant energy reflected from the first zone of the room; measuring, with the processor, a kill dose threshold based on germicidal radiation sensor input and air gap compensation.

Yet another object of the present disclosure is a system for room disinfection using germicidal radiation comprising one or more disinfection fixtures and an optional remotely mounted germicidal radiation sensor (remote sensor) operating in a communications network, the one or more disinfection fixtures comprising: a substantially rectangular housing having dimensions of approximately two feet in width and four feet in length; a first plurality of emitters coupled to the substantially rectangular housing, the first plurality of emitters operable to emit UV-C radiation at a wavelength of about 265 nanometers; a second plurality of emitters coupled to the substantially rectangular housing, the second plurality of emitters operable to emit near-UV radiation at a near-UV wavelength of about 405 nanometers; at least one visible light emitter coupled to the substantially rectangular housing; at least one, optional, germicidal radiation sensor coupled to the substantially planar array surface (alternatively, the system may employ a networked remote sensor directed to one or more target areas); a controller being housed in the substantially rectangular housing, the controller being operably engaged with the first plurality of emitters, the second plurality of emitters, the at least one visible light emitter, and the at least one germicidal radiation sensor; and, a remote interface, the remote interface being communicably engaged with the controller of the at least one portable UV-C disinfection apparatus, the optional remote sensor; and, a database, the database being communicably engaged with the controller and the remote interface.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

The above and other objects, features and advantages of the present disclosure will be more apparent from the following detailed description taken in conjunction with the accompanying drawings, in which:

FIG. 8 is a functional block diagram of the setup process of an embodiment of a hybrid germicidal irradiation disinfection apparatus;

FIG. 9 is a functional block diagram of the disinfection process of an embodiment of a hybrid germicidal irradiation disinfection apparatus; and, FIG. 10 is a functional block diagram illustrating the storing of data from the disinfection process of an embodiment of a hybrid germicidal irradiation disinfection apparatus.

DETAILED DESCRIPTION OF THE INVENTION

Figure 1:
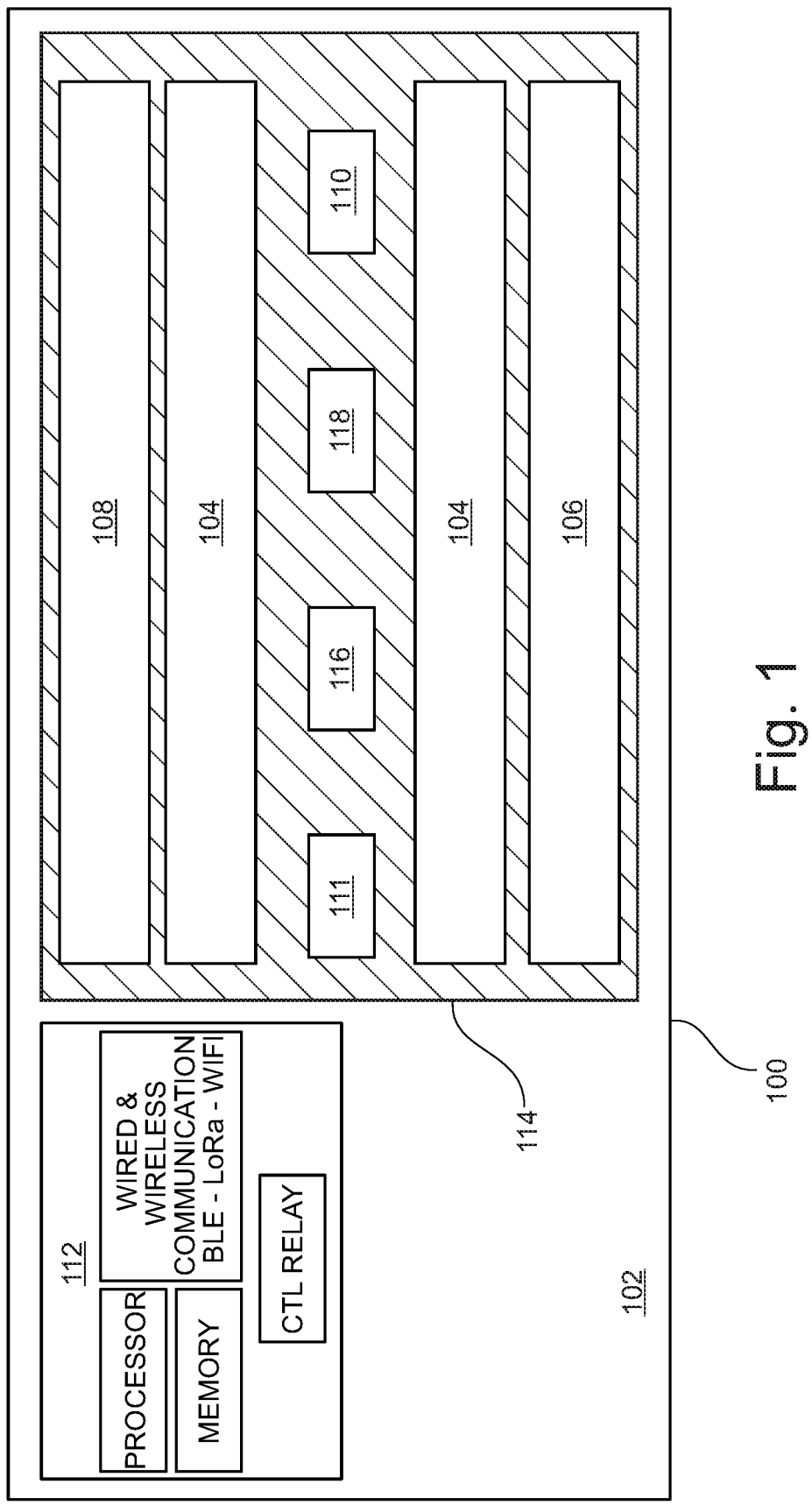
FIG. 1 is a perspective view of a hybrid germicidal irradiation disinfection apparatus in an embodiment of the present disclosure.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure further provide for a more cost-effective solution to retrofit overhead light fixtures with UV-C and near-UV emitters in hospital-wide deployments.

Referring now to FIG. 1, a diagrammatic representation of a hybrid germicidal irradiation disinfection apparatus (disinfection fixture) 100 is shown. According to an embodiment, disinfection fixture 100 is generally comprised of a fixture housing 102, a visible light emitter 104, a 265 nanometers (nm) UV-C emitter 106, a 405 nanometers (nm) near-UV emitter 108, a 265 nm germicidal radiation sensor (UV-C Sensor) 110, a 405 nm germicidal radiation sensor (Near-UV Sensor) 111, a controller 112, a UV transmittable lens 114, a ranging sensor 116, and an occupant sensor 118. According to an embodiment, fixture housing 102 contains the emitter and circuitry components, wiring, and installation fittings of disinfection fixture 100. Fixture housing 102 may be two feet by two feet or two feet by four feet in dimension. Fixture housing 102 should be configured such that it may be installed in a standard-sized commercial ceiling grid, and should be installing using standard commercial wiring. The standard sizing and wiring of fixture housing 102 enables disinfection fixture 100 to be easily retrofitted into hospitals and other commercial structures. Fixture housing 102 may be constructed of rigid or flexible material, such as plastic, metal, metal alloy, and the like. Alternatively, variations in the fixture housing 102 materials, emitters and construction dimensions may be altered as needed for a specific application (e.g. wall-mounting, free-hanging installation, outside of a ceiling grid). Fixture housing 102 is configured to house an electrical relay to at least one visible light emitter 104 and one or more 265 nm UV-C emitter 106 and/or one or more 405 nm near-UV emitter 108. Visible light emitter 104 should be of a spectrum and color temperature typically used for commercial interior lighting, for example 2650-kelvin. The disinfection fixture 100 provides dual functionality as both a commercial light source and a germicidal radiation emitter. UV-C emitters 106 and 405 nm emitters 108 are preferably UV-C LEDs and near-UV LEDs, respectively. In an alternative embodiment, UV-C emitters 106 and near UV emitters 108 are electronic gas-discharge lamps including but not limited to low-pressure mercury-vapor lamps, high-pressure mercury vapor lamps, xenon lamps, mercury-xenon lamps, pulsed-xenon lamps, and deuterium lamps. In another embodiment, UV-C emitters 106 and near UV emitters 108 may be CFL lamps and halogen lamps. UV-C 265 nm emitters 106 and 405 nm emitters 108 may be distributed in a linear arrangement and direct UV-C and near-UV radiation in a targeted or distributed beam, enabling higher intensity emission with less power consumption as compared to an omnidirectional bulb. The higher intensity generated by focusing a beam of germicidal radiation using a linear array, rather than an omnidirectional transmission generated by a mercury-vapor bulb or circular LED array, has the dual benefits of reducing exposure time in the dosage calculation and conserving energy. UV-C and near-UV emitters may be calibrated to various wavelength emissions within a known range of wavelengths that demonstrate strong disinfection effect.

As discussed above, emitters 106 and emitters 108 emit radiation at wavelengths of 265 nm and 405 nm respectively. Each wavelength displays its own kinetics of a kill curve for target microorganisms. It is anticipated that emitters 104 and emitters 106 may pulse emission in-phase (i.e. emit light at the same time), or out of phase (i.e. emit light at opposite times), or operate independently, which may modify the kinetics of each wavelength's respective kill curve such that a dual wavelength emission will reduce the overall time required to achieve a kill dose as compared to a single wavelength emission. Likewise, various modulation schema may be employed between emitters 104 and emitters 106 in order to optimize the kinetics of the kill curve for a given microorganism (e.g. viruses, bacteria, and spores); thereby reducing the amount of time required to achieve a kill dose for the target microorganism.

According to an embodiment, UV-C sensor 110, Near-UV sensor 111, ranging sensor 116 and occupant sensor 118 are coupled to a face portion of the fixture housing 102. Optionally, ranging sensor 116 and occupant sensor 118 may be combined into a single sensor or sensor suite. UV-C sensor 110 is a closed loop sensor operable to measure the amount of UV-C energy reflected from the target surface back to the UV-C sensor 110. Near-UV sensor 111 is also a closed loop sensor operable to measure the amount of near-UV energy reflected from the target surface back to the Near-UV sensor 111. UV-C sensor 110 and Near-UV sensor 111 may be a single sensor or an array of multiple sensors. UV-C sensor 110 and Near-UV sensor 111 may be a single dual-band sensor operable to measure radiation wavelengths of about 265 nm and about 405 nm. UV-C sensor 110 and Near-UV sensor 111 are operably engaged with controller 112 to communicate the amount of UV-C and near-UV radiation (single or dual band) collected by the sensor(s).

Controller 112 has a set of instructions stored thereon to measure a "kill dose" according to the amount of reflected UV-C and/or near UV radiation collected by UV-C sensor 114 and kill dose parameters stored in memory. Controller 112 may calibrate various kill dose thresholds depending on the specific disinfection application. For example, viruses may require a lower kill dose, while bacteria may require a higher kill dose, and spores may require yet a higher kill dose.

Controller 112 may operate in communication with ranging sensor 116 to more accurately measure a kill dose delivered from emitters 106 and/or emitters 108. The UV-C energy collected by UV-C sensor 110 might not accurately represent the amount of UV-C energy reflected by the target surface due to the distance, or air gap, between the target surface and UV-C sensor 110. This is due to the fact that germicidal radiation loses intensity as a function of distance travelled; therefore, the measured reflected energy at UV-C sensor 110 is less than the actual reflected energy received by the target surface as a function of the distance between the target surface and UV-C sensor 110. Ranging sensor 116 may be operably engaged with controller 112 to calculate an "air gap compensation" to virtually relocate UV-C sensor 110 to the nearest surface. This can be accomplished mathematically by correcting for the reduction in UV-C energy as a function of distance. Ranging sensor 116 may be comprised of, for example, one or more sensors capable of detecting the presence and location of objects within the sensor range without physical contact, such as sonic ranging, scanning ranging, and/or visible or infrared-based light sensors. Ranging sensor 116 is operably engaged to detect the distance to the nearest object in the zone of each UV-C sensor 110. Controller 112 may adjust the kill dose threshold of reflected energy received by UV-C sensor 110 in accordance with the distance input defined by ranging sensor 116. In the absence of ranging sensor 116, controller 112 may enable a manual input by a user to define the desired air gap adjustment.

As a safety precaution to prevent a user from exposure to UV-C radiation, occupant sensor 118 may be operably engaged with controller 112 to disengage emitter 106 when an occupant is detected in a room. As with ranging sensor 116, occupant sensor 118 may be comprised of, for example, one or more sensors capable of detecting the presence and location of objects within the sensor range without physical contact, such as sonic ranging sensors, scanning ranging sensors, and/or visible or infrared-based light sensors. Lens 114 covers the perimeter of fixture housing 102 and protects the emitters 104, 106 and 108 from debris and dust. Lens 114 may be constructed from any UV-C transmittable material, and may be configured as a Fresnel lens such that lens 114 may be substantially planar in shape.

Figure 2:
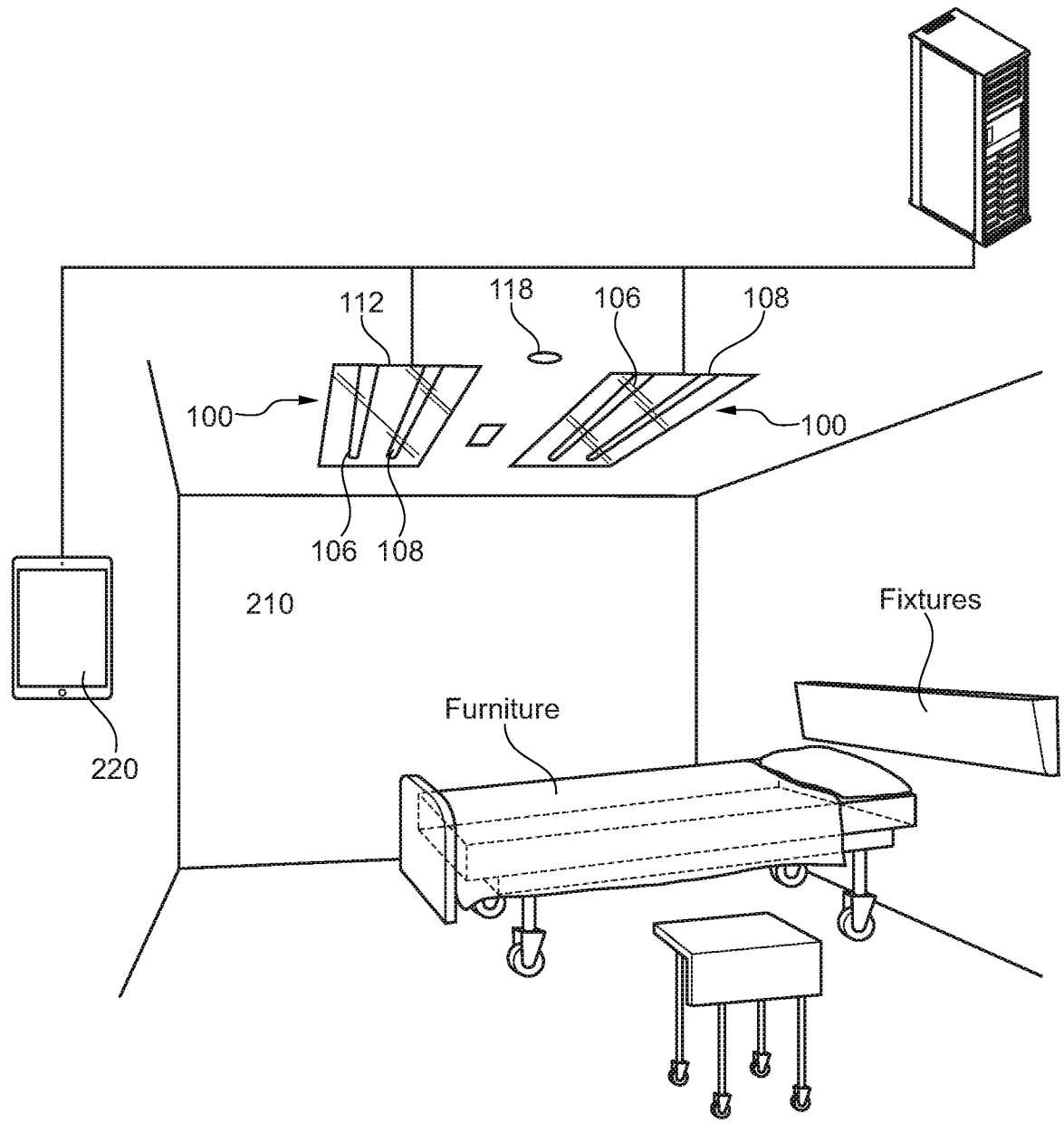
FIG. 2 is a system drawing of communication flow during a room disinfection by an embodiment of a hybrid germicidal irradiation disinfection apparatus.

Referring now to FIG. 2, a system drawing of communication flow during a disinfection cycle started via a remote interface is shown. According to an embodiment, disinfection fixture 100 administers germicidal radiation to a target zone via one or more emitters 106 and emitters 108. In a preferred embodiment, UV-C emitters 106 are calibrated to emit short wave UV-C radiation at a wavelength of 265 nm, and emitters 108 are calibrated to emit short wave near-UV radiation at a wavelength of 405 nm. Remote Interface 220 is networked to controller 112 via a wireline or wireless communication interface, such as Bluetooth or LoRa. Remote interface 220 may be a tablet computer, desktop computer, smart phone, laptop computer, wireless I/O device, and the like. Remote interface 220 associates a room identifier 210 with the disinfection fixture 100. A room identifier 210 may be a scanned barcode or RFID tag. This association ensures that all data collected during the disinfection cycle is attributed to the target room. Controller 112 receives the signal from remote interface 220 to begin the disinfection cycle. Occupant sensor 118 is activated to detect movement in the room. During this safety check, movement detected in the room will inhibit the initial ranging sensor scan. In the embodiment shown in FIG. 2, the occupant sensor 118 is alternatively affixed remotely to one of the ceiling panels in the target room.

Figure 3:
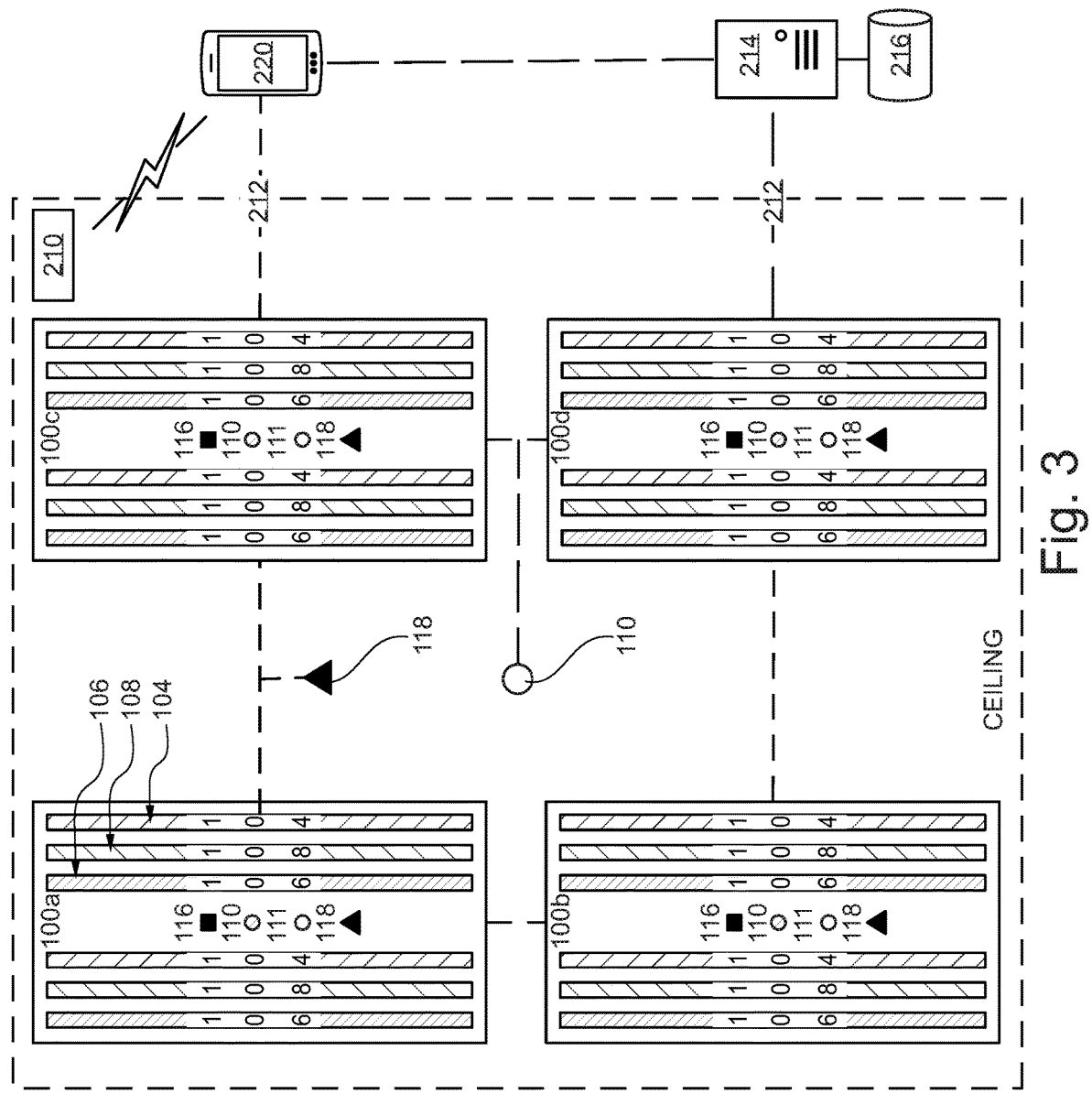
FIG. 3 is a system diagram of the integration of an embodiment of a hybrid germicidal irradiation disinfection apparatus, a remote germicidal radiation sensor, a remote interface and hospital server.

Referring now to FIG. 3, an illustrative system view of a networked implementation of multiple disinfection fixtures is shown. In an embodiment, multiple networked disinfection fixtures 100a-d are communicably linked to one another and one or more hospital systems via a LoRa, WiFi, or Bluetooth communication link. Alternatively, disinfection fixtures 100a-d may be hardwired and communicate through a hospital Ethernet network. Remote interface 220 sends a command to disinfection fixtures 100a-d to begin a room disinfection sequence. Each one of disinfection fixtures 100a-d is dedicated to a specific zone of the room and implements a safety protocol by signaling occupant sensor 118 to monitor each target zone for movement or occupants (i.e. infrared signatures). If no occupants are detected, the integrated disinfection fixtures 100a-d begin the disinfection cycle. The UV-C sensors measure the UV-C energy reflected from the target zone and/or the near-UV sensors measure the near-UV energy reflected from the target zone depending on the selected disinfection sequence. The ranging sensors measure the distance to the nearest object in the zone, and virtually relocate the germicidal radiation sensors to the location of the nearest object surface to compensate for the air gap between the surface of the nearest object and the surface of the germicidal radiation sensors (as discussed in FIGS. 4-6). Controller 112 continuously monitors germicidal sensor data against a predetermined kill dose threshold to determine whether a kill dose has been administered to the target zone. Once a target zone has received an effective kill dose, emitters 106 and/or 108 are disengaged or redirected to a different zone. The disinfection cycle is complete once all zones in the target room have received the designated radiation kill dose. Controller 112 sends a notification to remote interface 220 upon completion of the disinfection cycle. Remote interface 220 associates disinfection data with room ID 210. The disinfection data as well as other system data is stored in hospital server 214 and is accessible by remote interface 220.

Figure 4:
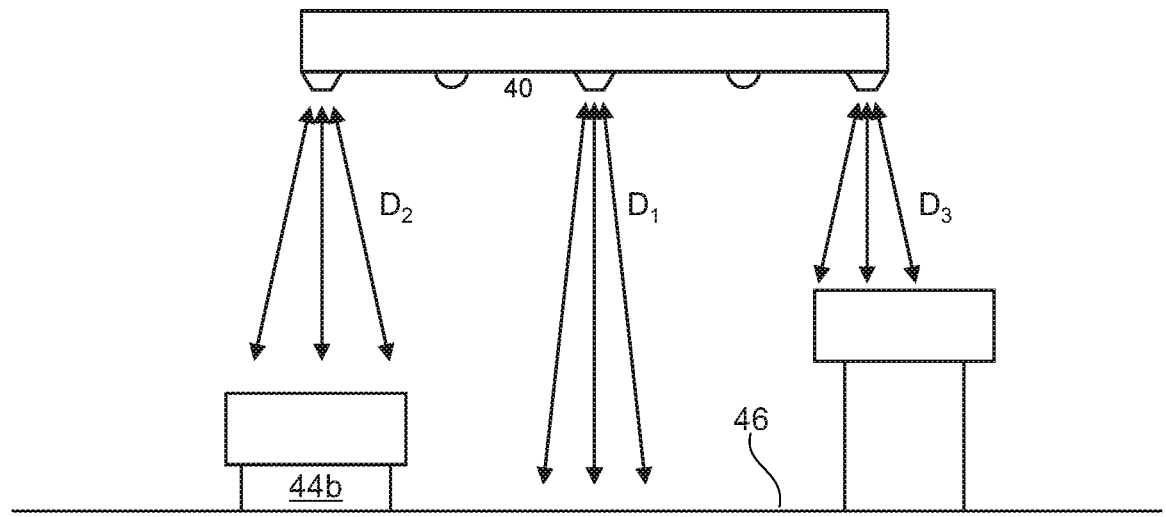
FIG. 4 is a functional diagram of a ranging sensor according to an embodiment.
Figure 5:
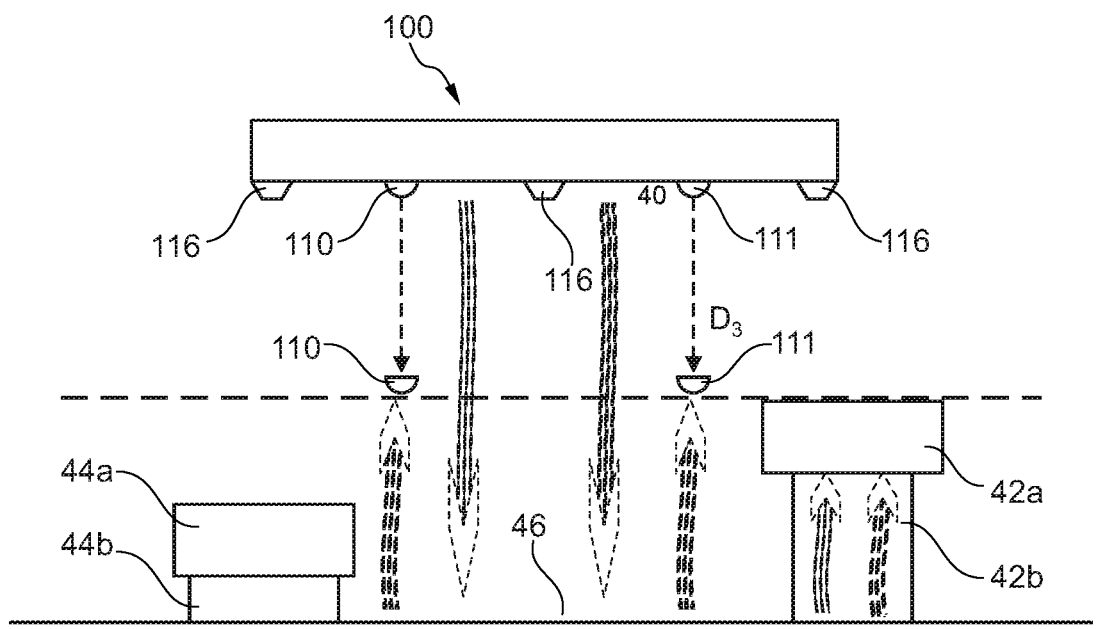
FIG. 5 is a functional diagram of an air gap compensation measurement (virtual germicidal radiation sensor location), according to an embodiment.

Referring now to FIGS. 4 and 5, a functional illustration of an air gap compensation calculation by disinfection fixture 100 is shown. According to an embodiment, ranging sensor(s) 116 measures the distance from disinfection fixture 100 surface 40 to the floor surface 46, $D_1$, and to the leading surface of the closest furniture and fixtures in the room 42a, $D_3$ and 44a, $D_2$. In this illustration, surface 42a at distance $D_3$ is the closest surface to disinfection fixture 100 and is used to define the air gap compensation setting for germicidal radiation sensors 110 and 111. The back side of the object, surface 42b (i.e. the "dark" side of the object relative to disinfection fixture 100) is disinfected by receiving germicidal radiation reflected back from the floor surface 46. As discussed above, a kill dose is measured by the amount of radiation reflected from the target surface to germicidal radiation sensors 110 and/or 111. The kill dose is measured using reflected radiation, rather than direct energy, in order to ensure that the dark side of surfaces in the target room (i.e. surfaces not receiving direct exposure of germicidal radiation) are sufficiently disinfected. The amount of reflected radiation can be accurately measured from the leading edge of the closest object in the room 42a to infer the dosage received by the dark side of object 42b.

Referring now to FIG. 5, the distance $D_3$ represents the air gap between germicidal radiation sensors 110 and 111 and the leading edge of the closest object in the room 42a. The intensity of the reflected radiation is reduced between $D_3$ and $D_1$, as the intensity of radiation diminishes with distance. Therefore, measuring a kill dose at surface 40 results in an over measurement of radiation, which in turn results in overexposure of germicidal radiation and increased time for disinfection fixture 100 to complete a disinfection cycle. Disinfection fixture 100 mitigates over-exposure and minimizes disinfection time by virtually relocating germicidal radiation sensors 110 and/or 111 to surface 42a by executing an air gap compensation algorithm. This enables disinfection fixture 100 to emit the minimum required amount of germicidal irradiation necessary for an effective kill dose per the selected disinfection cycle.

Figure 6:
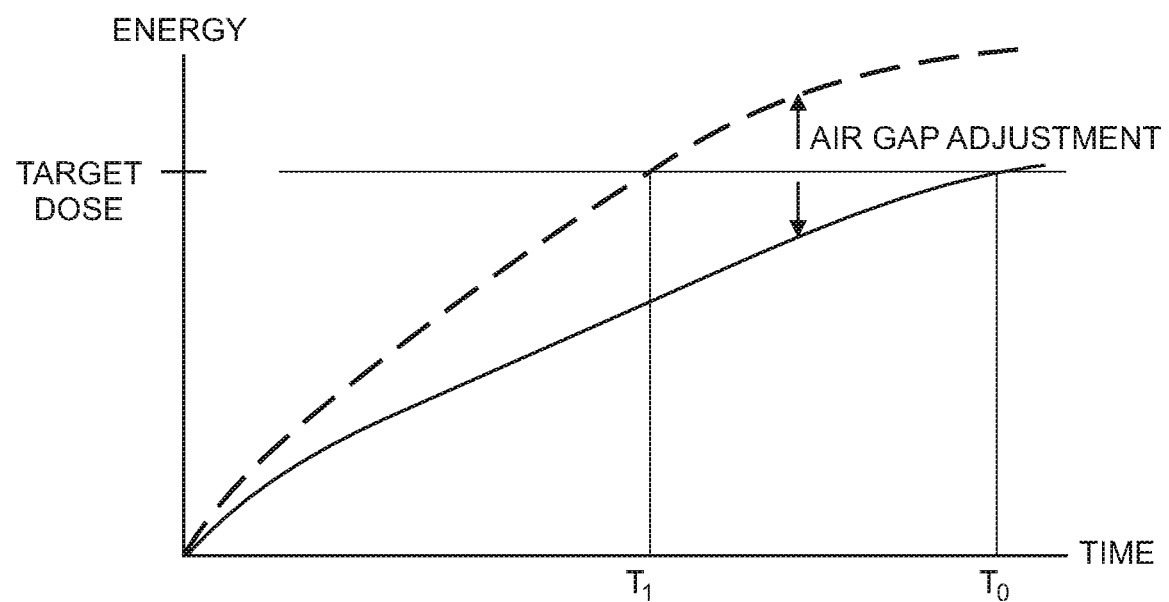
FIG. 6 is a plot of a target dose calculation, as calculated with and without compensation for air gap.

FIG. 6 further illustrates the above concepts of FIG. 5 by plotting the reflected energy received by germicidal radiation sensor 110 (on the y-axis) as a function of time (on the x-axis) in order to reach a target dose of reflected energy. Where UV-C sensors 110 have not been virtually relocated to compensate for air gap, the time required to reach an effective kill dose is shown on the graph as $T_0$. Where UV-C sensors 110 have been virtually relocated to compensate for air gap, the time required to reach an effective kill dose is shown on the graph as $T_1$. The delta between $T_0$ and $T_1$ represents the amount of time saved during the disinfection cycle when compensating for air gap between the germicidal sensor and the location of the nearest object in the zone.

Figure 7:
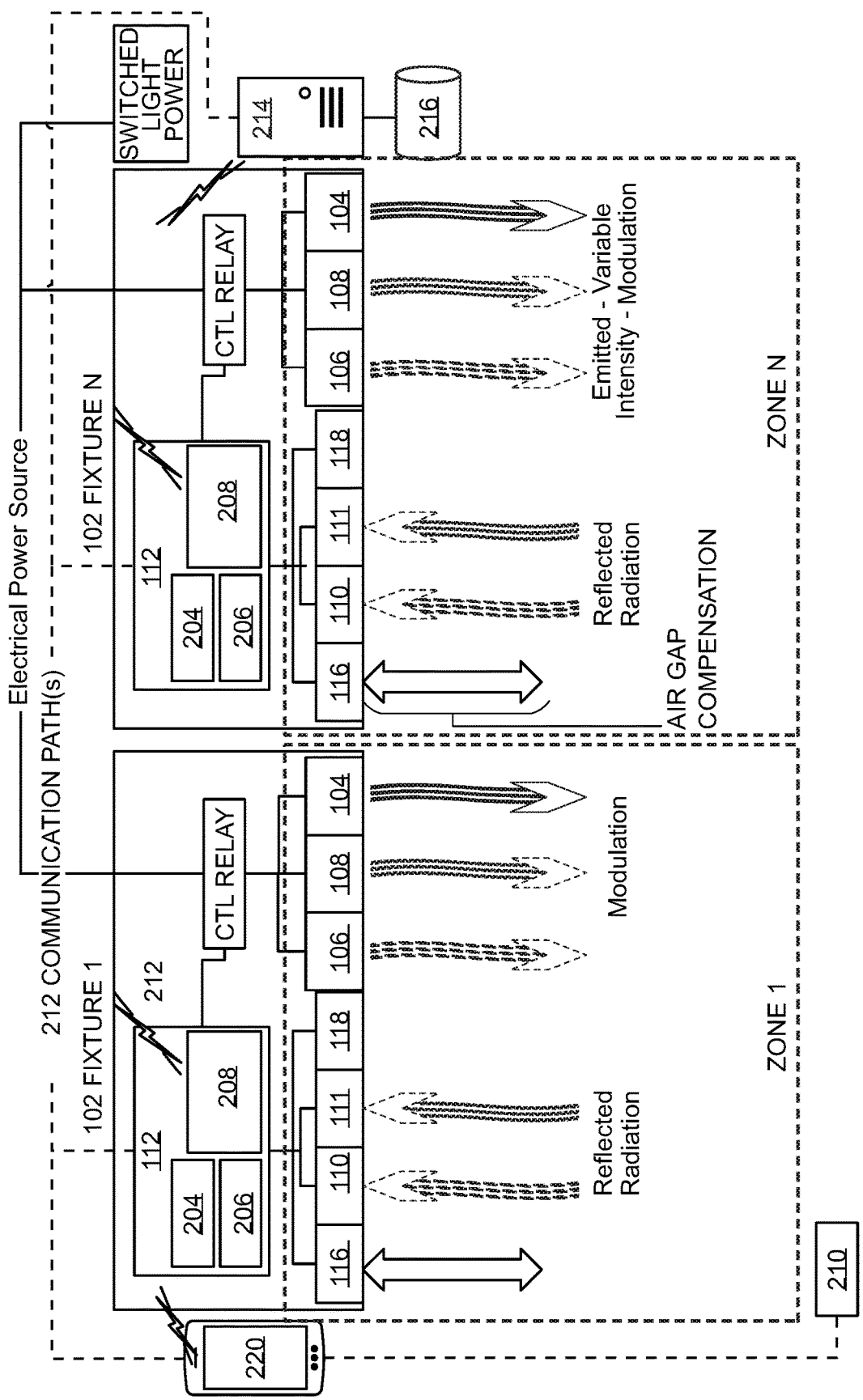
FIG. 7 is a functional diagram of an embodiment of a hybrid germicidal irradiation disinfection apparatus.

Referring now to FIG. 7, a system diagram of a ceiling-mounted disinfection fixture is shown. According to an embodiment, disinfection fixture 100 administers germicidal radiation to a target zone via one or more UV-C emitters 106 and one or more near-UV emitters 108. In a preferred embodiment, as mentioned above, UV-C emitters 106 are calibrated to emit short wave UV-C radiation at a wavelength of 265 nm, and near-UV emitters 108 are calibrated to have a wavelength emission of 405 nm. Remote interface 220 is communicably engaged with controller 112 via a wireless communication interface, such as Bluetooth or WiFi. Remote interface 220 may be a tablet computer, smart phone, laptop computer, wireless I/O device, and the like. Remote interface 220 associates a room identifier 210 with a target room for disinfection. Remote interface 220 may include a user workflow configured to validate that a target room is prepped properly for disinfection and that all the steps in the disinfection workflow have been completed. A room identifier 210 may be a scanned barcode or RFID tag. Remote interface 220 communicates a request to begin a disinfection cycle to controller 112. Processor 204 processes the request to begin a disinfection cycle. Processor 204 executes instructions for ranging sensor 116 to scan a target Zone 1 to determine the closest object in the zone. The data from ranging sensor 116 is stored in memory 206, along with room ID 210. Processor 204 executes instructions to measure air gap compensation to calibrate UV-C sensor 110 according to the data from ranging sensor 116. Processor 204 executes instructions to initiate UV-C emitters 104 and/or near-UV emitters 106 to emit germicidal radiation to target Zone 1 thru N. Radiation reflected from the target Zone 1 through N is reflected back to array housing 102 and is collected by UV-C sensor 110. UV-C sensor 110 sends dosage data to processor 204. Processor 204 executes instructions to measure a kill dose according to UV-C reflectivity data and air gap compensation variables. Once a threshold dosage value has been received by UV-C sensor 110, processor 204 executes instructions to discontinue radiation emission by emitters 106. In parallel the same closed-loop disinfection process may be performed, depending on the selected disinfection cycle, by processor 204 for the desired dose of near-UV germicidal irradiation using ranging sensor 116, near-UV sensor 111 and emitters 108.

Processor 204 executes instructions to store dosage data from each zone in memory 206. The dosage data is time stamped, and communicated to hospital server 214 using wireless communication chip set 208 via hospital network 212. Hospital server 214 stores information retrieved from controller 112 in hospital database 216. This information can be utilized by hospital server 214 to determine the health of the hospital, audit cleaning activities, as well as monitor the health and status of a facility wide deployment. Communication chip set 208 may be a LoRa chipset, and hospital network 212 may be configured as a low power wide area network (LPWAN) to reduce burden on the hospital's Wi-Fi network. Processor 204 may communicate a confirmation to remote interface 220 to confirm disinfection of the target room is complete.

Referring now to FIG. 8, a block diagram illustrating how to set up a disinfection fixture is shown. According to an embodiment, the disinfection fixture(s) may be retrofitted into a ceiling grid by uninstalling an existing fluorescent light fixture(s) 502 and installing one or more disinfection fixtures 504. The installed disinfection fixtures may be communicably coupled with the hospital server 506 through Bluetooth or LoRa utilizing a wireless chip in the controller unit or alternatively the disinfection fixtures may be hard-wired to a network (e.g. Ethernet). The hospital server associates each disinfection fixture with a specific Room ID 508 and all data regarding room disinfection such as fixture placement and germicidal irradiation dosage calculation is saved under an association with specific room ID 508. This information is saved in the disinfection fixture's memory and may be accessed and saved on the hospital server. Alternatively, the disinfection fixtures memory may be accessed by a remote interface. The disinfection cycle may be engaged by a remote interface such as a tablet computer, laptop, or smartphone by establishing a wireless communication link (such as Bluetooth, WiFi, or LoRa) with the controller of the disinfection fixture 510. The remote interface links disinfection fixtures with the same room ID to an assigned room 512.

Referring now to FIG. 9, a block diagram illustrating the steps of the disinfection cycle is shown. A remote interface such as a tablet, smartphone, or laptop sends a request for disinfection 602 to the disinfection fixture(s) via a communications network. An occupant sensor verifies the target room is unoccupied, and transmits a success message to a processor associated with a disinfection fixture 604. One or more ranging sensors measures the distance to the closest surface in the zone, and the processor computes an air gap compensation parameter for the germicidal radiation sensor 606. LED emitters emit radiation at wavelengths of 265 nm and/or 405 nm to target area 608. Emitters may pulse emission in-phase (i.e. emit light at the same time), or out of phase (i.e. emit light at opposite times), or deliver single mode germicidal radiation depending on the selected disinfection cycle. Emitted radiation is reflected back from surfaces in the zone to germicidal sensors, which measure the reflected dual band germicidal radiation 610 and transmit the data to the processor. The processor executes instructions to calculate a kill dose for the target zone based on the sensor data and air gap compensation algorithm 612. Once a zone has received a kill dose, the controller disengages the emitters and ends the zone radiation 614 in accordance with the selected disinfection mode.

Embodiments of the present disclosure provide for multiple modes of operation, including normal mode, in which the disinfection fixture as shown and described above may operate as a standard lighting fixture to emit non-UV visible light to illuminate a room, and several disinfection modes depending on the desired level of disinfection, the organism involved, and the occupation of the target space. Two such modes may include: Disinfection and Sustainment. The Disinfection Mode follows the flow outlined above by FIG. 9. Disinfection Mode is selected when the target room is unoccupied and standard cleaning has been performed. Both germicidal emitters 106 and 108 may be energized and the visible light emitters 104 may be depowered.

Sustainment Mode may be selected after the room has been disinfected to maintain a desired level of disinfection or when the room is occupied by a patient with a compromised immune system or active infection such as MRSA. In this mode the visible light emitters will operate via the remote interface 220. The output level (brightness and intensity) of the visible light emitters 104 may be varied by pulse-width modulation or active current control in response to commands from the remote interface 220. The UV-C Emitters 106 will remain off as the room is occupied. The near-UV emitters 108 may remain continuously on thereby providing continuous air and surface disinfection. The output level of the near-UV emitters 108 may be varied by pulse-width modulation or active current control in response to commands from the remote interface 220.

Referring now to FIG. 10, a block diagram illustrating a method of storing dosage data associated with a room disinfection is shown. According to an embodiment, the processor communicates all dosage data related to a room disinfection to be stored in memory of the controller 702. The room dosage data is time-stamped 704 and associated with a room ID in a database. The time-stamped dosage information may be communicated to a hospital server 706 via a hospital network. The hospital server associates the time-stamped dosage information with the room ID of the disinfection fixtures 708. The time-stamped dosage data may also be accessed by or sent as a notification to a remote interface 710. This information can be utilized by quality control to determine the health of the hospital, as well as monitor the health and status of a facility wide deployment.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A fixed position hybrid germicidal irradiation disinfection apparatus comprising:
 a rectangular housing configured to be coupled to a standard commercial lighting fixture fitting and electrical wiring;
 a first plurality of emitters coupled to the rectangular housing, the first plurality of emitters operable to emit UV-C radiation at a wavelength of 265 nanometers;
 a second plurality of emitters coupled to the rectangular housing, the second plurality of emitters operable to emit near-UV radiation at a wavelength of 405 nanometers;
 a controller housed in the rectangular housing, the controller being operably engaged with the first plurality of emitters, the second plurality of emitters, and at least one visible light emitter; and
 at least one ranging sensor coupled to the rectangular housing and operably configured to provide a ranging input to the controller, the controller being configured to calculate a virtual air gap adjustment parameter in response to the ranging input and to control an emission from the first plurality of emitters and the second plurality of emitters according to the virtual air gap adjustment parameter, and,
 wherein the first plurality of emitters and the second plurality of emitters are configured to pulse emissions of UV-C radiation and near-UV radiation, respectively, in phase and out of phase.

2. The fixed position hybrid germicidal irradiation disinfection apparatus of claim 1, wherein the controller is configured to dynamically control an emission intensity of the first plurality of emitters, the second plurality of emitters, and the at least one visible light emitter.

3. The fixed position hybrid germicidal irradiation disinfection apparatus of claim 1, wherein the at least one visible light emitter is coupled to the rectangular housing.

4. The fixed position hybrid germicidal irradiation disinfection apparatus of claim 1, wherein the first plurality of emitters and the second plurality of emitters are selected from the group consisting of LEDs, electronic gas-discharge lamps, CFL lamps, and halogen lamps.

5. A method for room disinfection using germicidal radiation comprising:
    installing, in an interior ceiling grid, the fixed position hybrid germicidal irradiation disinfection apparatus of claim 1,
    measuring, with the ranging sensor, a distance to an object that is closest to the hybrid germicidal irradiation disinfection apparatus in the room;
    calculating, with the controller, an air gap compensation variable in response to the ranging sensor measurement;
    delivering, with the first plurality of emitters and the second plurality of emitters, dual band germicidal radiation to a target zone of the room;
    receiving, with the at least one ranging sensor, an amount of radiant energy reflected from the target zone of the room; and,
    measuring, with a processor, a kill dose threshold based on the amount of radiant energy reflected from the target zone of the room, a distance between the target zone and the at least one ranging sensor, and the air gap compensation variable calculated by the controller in response to the ranging sensor measurement.

6. The method for room disinfection using germicidal radiation of claim 5, further comprising:
    verifying, with an occupant sensor, the target zone is unoccupied.

7. The method for room disinfection using germicidal radiation of claim 5, further comprising:
    storing, in non-volatile memory of the controller, the kill dose threshold related to room disinfection; and,
    communicating, with a wireless communication interface, the kill dose threshold to a computer system.

8. The method for room disinfection using germicidal radiation of claim 5, wherein the first plurality of emitters and the second plurality of emitters are configured to pulse emission in-phase and out of phase.

9. The method for room disinfection using germicidal radiation of claim 5, wherein the first plurality of emitters and the second plurality of emitters are selected from the group consisting of LEDs, electronic gas-discharge lamps, CFL lamps, and halogen lamps.

10. A system for room disinfection using germicidal irradiation comprising:
    one or more hybrid germicidal irradiation disinfection apparatus operating in a communications network, the one or more hybrid germicidal irradiation disinfection apparatus comprising:
        a rectangular housing;
        a first plurality of emitters coupled to the rectangular housing, the first plurality of emitters operable to emit UV-C radiation at a wavelength of 265 nanometers;
        a second plurality of emitters coupled to the rectangular housing, the second plurality of emitters operable to emit near-UV radiation at a wavelength of 405 nanometers;
        at least one visible light emitter coupled to the rectangular housing;
        at least one UV-C sensor coupled to the rectangular housing, wherein the at least one UV-C sensor is a closed loop sensor configured to measure an amount of UV-C radiation reflected from a target surface back to the at least one UV-C sensor;
        at least one near-UV sensor coupled to the rectangular housing, wherein the at least one near-UV sensor is a closed loop sensor configured to measure an amount of near-UV radiation reflected from a target surface back to the at least one near-UV sensor;
        at least one ranging sensor coupled to the rectangular housing;
        a controller housed in the rectangular housing, the controller being operably engaged with the first plurality of emitters, the second plurality of emitters, the at least one visible light emitter, the at least one UV-C sensor, the at least one near-UV sensor, and the at least one ranging sensor,
            wherein the at least one ranging sensor is configured to provide a ranging input to the controller, the controller being configured to calculate a virtual air gap adjustment parameter in response to the ranging input and to control an emission from the first plurality of emitters and the second plurality of emitters according to the virtual air gap adjustment parameter;
        a remote interface, the remote interface being communicably engaged with the controller of the one or more hybrid germicidal irradiation disinfection apparatus; and,
        a database, the database being communicably engaged with the controller and the remote interface.

11. The system for room disinfection using germicidal irradiation of claim 10, wherein the first plurality of emitters and the second plurality of emitters are selected from the group consisting of LEDs, electronic gas-discharge lamps, CFL lamps, and halogen lamps.

12. The system for room disinfection using germicidal irradiation of claim 10, wherein the remote interface is selected from the group consisting of a tablet computer, a smart phone, and a laptop computer.

13. The system for room disinfection using germicidal irradiation of claim 10, wherein the one or more hybrid germicidal irradiation disinfection apparatus further comprises at least one occupant sensor coupled to the rectangular housing, the at least one occupant sensor being operably engaged with the controller.

14. The system for room disinfection using germicidal irradiation of claim 10, wherein the controller is operable to dynamically control an emission intensity of the first plurality of emitters, the second plurality of emitters, and the at least one visible light emitter.

15. The system for room disinfection using germicidal irradiation of claim 10, wherein the database is configured to store a disinfection status and disinfection log associated across a plurality of individually identified rooms.

16. The system for room disinfection using germicidal irradiation of claim 10, wherein the first plurality of emitters and the second plurality of emitters are configured to pulse emissions of radiation in phase and out of phase.

17. The system for room disinfection using germicidal irradiation of claim 16, wherein the first plurality of emitters and the second plurality of emitters are configured to independently emit radiation so as to produce a dual wavelength emission.

18. The system for room disinfection using germicidal irradiation of claim 10, further comprising a lens of a UV-C transmittable material coupled to a perimeter of the rectangular housing.

19. The fixed position hybrid germicidal irradiation disinfection apparatus of claim 1, further comprising a lens of a UV-C transmittable material coupled to a perimeter of the rectangular housing.

20. The fixed position hybrid germicidal irradiation disinfection apparatus of claim 1, further comprising:

at least one UV-C sensor coupled to the rectangular housing, wherein the at least one UV-C sensor is a closed loop sensor operable to measure an amount of UV-C radiation reflected from a target surface back to the at least one UV-C sensor; and at least one near-UV sensor coupled to the rectangular housing, wherein the at least one near-UV sensor is a closed loop sensor operable to measure an amount of near-UV radiation reflected from a target surface back to the at least one near-UV sensor.

* * * * *